United States Patent
Koh

(10) Patent No.: US 8,343,059 B1
(45) Date of Patent: Jan. 1, 2013

(54) IDENTIFYING LEFT ATRIAL PRESSURE ELEVATION BY MEANS OF A RESPIRATORY COMPONENT

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 1192 days.

(21) Appl. No.: 11/678,401

(22) Filed: Feb. 23, 2007

(51) Int. Cl.
*A61B 5/02* (2006.01)
*A61B 5/08* (2006.01)

(52) U.S. Cl. ......................................... 600/484; 600/486

(58) Field of Classification Search ................... 600/484, 600/486, 561; 607/2
See application file for complete search history.

(56) References Cited

U.S. PATENT DOCUMENTS

| | | | |
|---|---|---|---|
| 4,567,899 A * | 2/1986 | Kamens et al. | 600/493 |
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,181,517 A * | 1/1993 | Hickey | 600/486 |
| 5,391,190 A * | 2/1995 | Pederson et al. | 607/23 |
| 5,466,254 A | 11/1995 | Helland | |
| 5,476,483 A | 12/1995 | Bornzin et al. | |
| 5,954,752 A * | 9/1999 | Mongeon et al. | 607/6 |
| 6,299,582 B1 * | 10/2001 | Brockway et al. | 600/484 |
| 7,862,513 B2 * | 1/2011 | Eigler et al. | 600/486 |
| 2004/0147969 A1 * | 7/2004 | Mann et al. | 607/17 |

* cited by examiner

*Primary Examiner* — Michael Kahelin
*Assistant Examiner* — Michael R Bloch

(57) ABSTRACT

A signal indicative of left atrial pressure in the heart of a patient is analyzed to identify a signal component that is related to the respiration of the patient. An indication relating to the left atrial pressure may be generated based on the presence, absence, or magnitude of the respiratory component. In some embodiments the indication may be used to indicate high left atrial pressure. In some embodiments the indication may be used to indicate heart failure. In some embodiments the indication may be used in conjunction with verifying the operation of a left atrial pressure sensor. In the event of high left atrial pressure or an incorrect pressure reading an appropriate warning may be generated. In the event of an incorrect pressure reading the left atrial pressure sensor may be recalibrated.

14 Claims, 5 Drawing Sheets ns that may be performed to generate an indication relating
IDENTIFYING LEFT ATRIAL PRESSURE ELEVATION BY MEANS OF A RESPIRATORY COMPONENT

TECHNICAL FIELD

This application relates generally to cardiac devices and procedures, and to detecting a respiratory component in a left atrial pressure signal.

BACKGROUND

When a person's heart does not function normally due to, for example, a genetic or acquired condition, various treatments may be prescribed to correct or compensate for the condition. For example, pharmaceutical therapy may be prescribed for a patient or a pacemaker or similar device may be implanted in the patient to improve the function of the patient's heart.

In conjunction with such therapy it may be desirable to detect conditions in or apply therapy to one or more chambers of the heart. For example, the health of many patients who have had some form of heart failure (e.g., a heart attack) may deteriorate over time due to progressive failure of the heart. To compensate for the reduction in heart function due to damaged heart tissue, the walls of the heart wall may thicken thereby enabling the heart to pump harder. The resulting enlargement of the heart, however, tends to reduce the ejection fraction of the heart. Progressive heart failure also may affect the timing of contractions in the heart. For example, the normally coordinated pumping of the right ventricle and the left ventricle may become unsynchronized.

The problems caused by progressive heart failure may eventually lead to acute decompensation and associated pulmonary-related conditions. For example, when the function of the left ventricle is compromised (e.g., the left ventricle ejects less blood), the pressure in the left atrium may rise due to a buildup in fluid returning from that portion of the venous system. The rise in left atrial pressure may, in turn, cause fluid to accumulate in the patient's lungs (a condition known as pulmonary edema). Fluid accumulation in the lungs may impair the delivery of oxygen to and the elimination of carbon dioxide from the cardiovascular system and cause hyperventilation or other breathing difficulties, thereby increasing the oxygen demand of the patient. This, in turn, may lead to the patient experiencing shortness of breath or other respiratory problems. If left untreated, such a condition may further exacerbate heart failure.

In view of the above, a rise in left atrial pressure has been proposed as a potential indicator of left ventricular failure. To this end, it had been proposed to implant a pressure sensor in the left atrium. Access to the left atrium may be obtained by initially routing a lead into the right atrium using well known techniques and then routing the lead through the septal wall that separates the right atrium from the left atrium.

In practice, a pressure sensor may need to be calibrated on a regular basis to maintain the accuracy of the corresponding pressure readings. For example, the pressure reading provided by the sensor in response to a given pressure may change over time due to limitations in the design and construction of the sensor (a condition known as sensor drift). To account for this problem, a sensor may be employed in conjunction with a compensation mechanism. For example, the compensation mechanism may automatically calibrate the pressure readings provided by the sensor by comparing the pressure reading with a known pressure such as ambient pressure.

In practice, a typical implanted pressure sensor may not be automatically calibrated in this manner due to the relative difficulty of readily obtaining access to ambient pressure to provide a reference pressure. Consequently, there is a need for improved techniques for detecting left atrial pressure.

SUMMARY

A summary of sample aspects and/or embodiments of an apparatus constructed or a method practiced according to the invention follows. For convenience, one or more embodiments of an apparatus constructed or a method practiced according to the invention may be referred to herein simply as an "embodiment" or "embodiments."

Some embodiments relate to determining pressure in the left atrium of the heart of a patient. To this end, an apparatus or method may determine whether a signal indicative of left atrial pressure includes a signal component that is related to the respiration of the patient. An indication relating to the left atrial pressure may then be generated based on the presence, absence, or magnitude of the respiratory component.

In some embodiments a sensor implanted in the left atrium generates signals indicative of left atrial pressure. The signals are then processed to identify a respiratory component and, in some embodiments, the amplitude of any respiratory component is analyzed. Based on these operations, an indication relating to the left atrial pressure is generated.

In some embodiments the indication may be used to indicate high left atrial pressure. For example, the absence of a respiratory component or a reduction in the amplitude of a respiratory component may indicate that the left atrial pressure has increased to such an extent that the patient's respiration can no longer modulate the pressure in the left atrium to a significant degree. In conjunction with such an indication an appropriate warning may be generated. In addition, in some embodiments therapy may be provided to the patient or a previously prescribed therapy may be modified.

In some embodiments the indication may be used to indicate heart failure. For example, if the pressure in the left atrium remains high for a given period of time, a heart failure indication (e.g., in conjunction with a warning signal) may be generated and, in some cases, appropriate therapy may be provided to the patient.

In some embodiments the indication may be used in conjunction with verifying the operation of a left atrial pressure sensor. For example, as discussed above the absence of a respiratory component or a reduction in the amplitude of a respiratory component may indicate that there has been an increase in left atrial pressure. In conjunction with such an indication, the pressure measurement readings from the sensor may be analyzed to determine whether the readings correspond to the increased left atrial pressure. In the event of an incorrect pressure reading an appropriate warning may be generated and, in some embodiments, the left atrial pressure sensor may be recalibrated.

BRIEF DESCRIPTION OF THE DRAWINGS

These and other features, aspects and advantages that may relate to the invention will be more fully understood when considered with respect to the following detailed description, appended claims and accompanying drawings, wherein:

Figure 1:
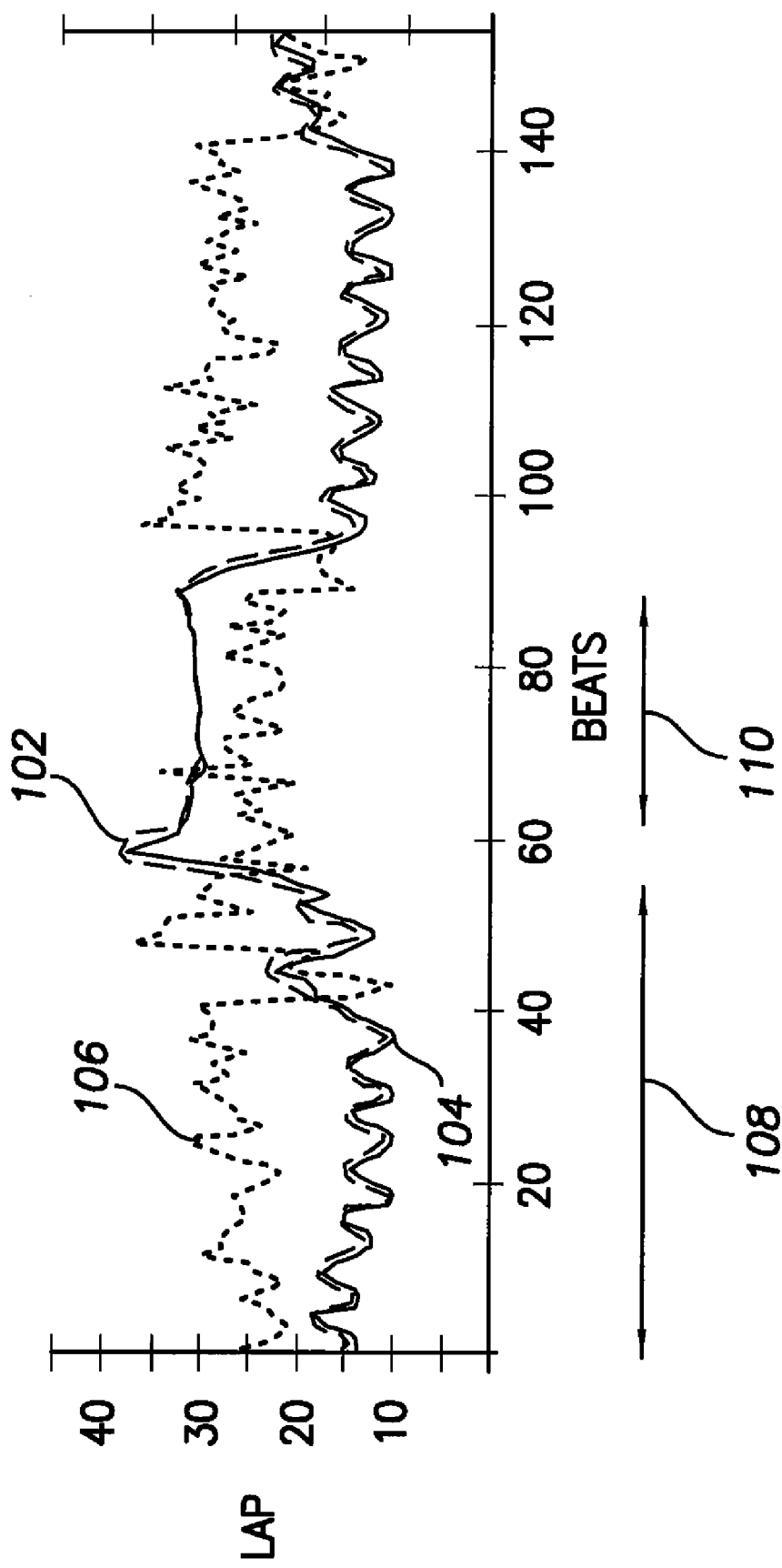
FIG. 1 is a simplified diagram illustrating an example of respiration modulation of a left atrial pressure signal.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented or a method practiced using other structural or functional details in addition to or other than the structural and/or functional details set forth in any disclosed embodiment(s).

Under normal conditions the pressure in the left atrium of a heart of a patient may fluctuate due to one or more external influences. For example, the respiration of the patient may cause slight changes in the left atrial pressure as a result of the external force applied on the left atrium by the gas/diaphragm pressure of the lungs. That is, the pressure in the left atrium will repeatedly increase or decrease slightly as the patient repeatedly inhales and exhales. Hence, the respiratory pattern of the patient effectively modulates the left atrial pressure.

FIG. 1 depicts several simplified waveforms 102, 104, and 106 that illustrate this relationship. The vertical axis of FIG. 1 represents left atrial pressure ("LAP") in mmHg. The horizontal axis of FIG. 1 relates to time as quantified by a number of beats of the heart. Thus, assuming a heart rate on the order of 60 beats per minute, the waveforms in FIG. 1 represent approximately two minutes in time.

The waveform 102 represents left atrial pressure measured over this time period. In particular, the waveform 102 relates to samples of maximum left atrial pressure taken over the time period. The waveform 102 thus illustrates a left atrial pressure signal that may be generated by a left atrial pressure sensor.

The waveform 104 also represents a left atrial pressure signals. In this case, however, the waveform 104 relates to samples of minimum left atrial pressure taken over the time period of FIG. 1.

The waveform 106 represents a cardiogenic impedance signal measured over the time period. Such a signal may be measured substantially across the left atrium using, for example, a left ventricle tip electrode and a right atrial tip electrode (discussed in more detail below) to generate constant current signals and sense resulting voltage signals. A typical detected cardiogenic impedance signal includes a respiratory component due to the relative proximity of the lungs to the electrodes. Thus, the waveform 106 is depicted as being modulated by a respiratory component (the smaller peaks and valleys throughout the waveform 106).

FIG. 1 illustrates that the waveforms 102 and 104 also include a similar respiratory modulation over a portion of the waveforms represented by line 108 (corresponding approximately to beats 1 through 55). That is, the small peaks and valleys of the waveforms 102 and 104 illustrate a respiratory signal component of a measured left atrial pressure signal. As discussed above, this respiratory component may be caused by the effect on the left atrium of the movement associated with the lungs.

The portion 108 of FIG. 1 illustrates a time period where the left atrial pressure is at or near a relatively normal value. For example, the average value of the left atrial pressure during this time period is on the order of 13 to 17 mmHg.

FIG. 1 also illustrates an increase in left atrial pressure during the time period represented by beats 55-60. Over a portion of the waveforms represented by line 110 (corresponding approximately to beats 62 through 90) the average value of the left atrial pressure is on the order of 30 mmHg.

During the time period 110 it may be seen that the left atrial pressure signal (e.g., waveform 102 or 104) is not modulated to any appreciable degree by a respiratory component. That is, during the time period 110 the left atrial pressure has risen to such an extent (e.g., above 20 mmHg) that the pressure is not influenced to any significant degree by the external force associated with the respiration of the patient.

Based on the above relationships, a determination may be made relating to the magnitude of left atrial pressure. For example, a left atrial pressure signal may be analyzed to determine whether the signal includes a respiratory component or to determine whether there have been any changes in the amplitude of a respiratory component of the signal. In the event the left atrial pressure signal does not include a respiratory component or in the event of a decrease in the amplitude of the respiratory component, a determination may be made that the magnitude of the pressure in the left atrium is approximately equal to the pressure corresponding to portion 110 rather than the pressure corresponding to portion 108. In other words, the amplitude of the respiratory component may be used to determine whether the pressure in the left atrium is within a normal range or is higher than normal.

In some embodiments minimum and maximum left atrial pressure measurements may be compared to determine whether left atrial pressure is at an elevated level (e.g., a level associated with a negligible respiratory component). For example, during the time period 108 in FIG. 1 there is a noticeable difference between the magnitudes of maximum left atrial pressure waveform 102 and the minimum left atrial pressure waveform 104. In contrast, during much of the time period 110 the magnitudes of the waveforms 102 and 104 are substantially the same. Hence, the difference between the waveforms 102 and 104 (e.g., running averages of the corresponding pressure signals) may be compared with a threshold difference value to determine whether the left atrial pressure is at an elevated level. In other words, based on such a comparison it may be determined whether the pressure in the left atrium is within a normal range (e.g., on the order of the pressures corresponding to portion 108) or is higher than normal (e.g., on the order of the pressures corresponding to portion 110).

Figure 2:
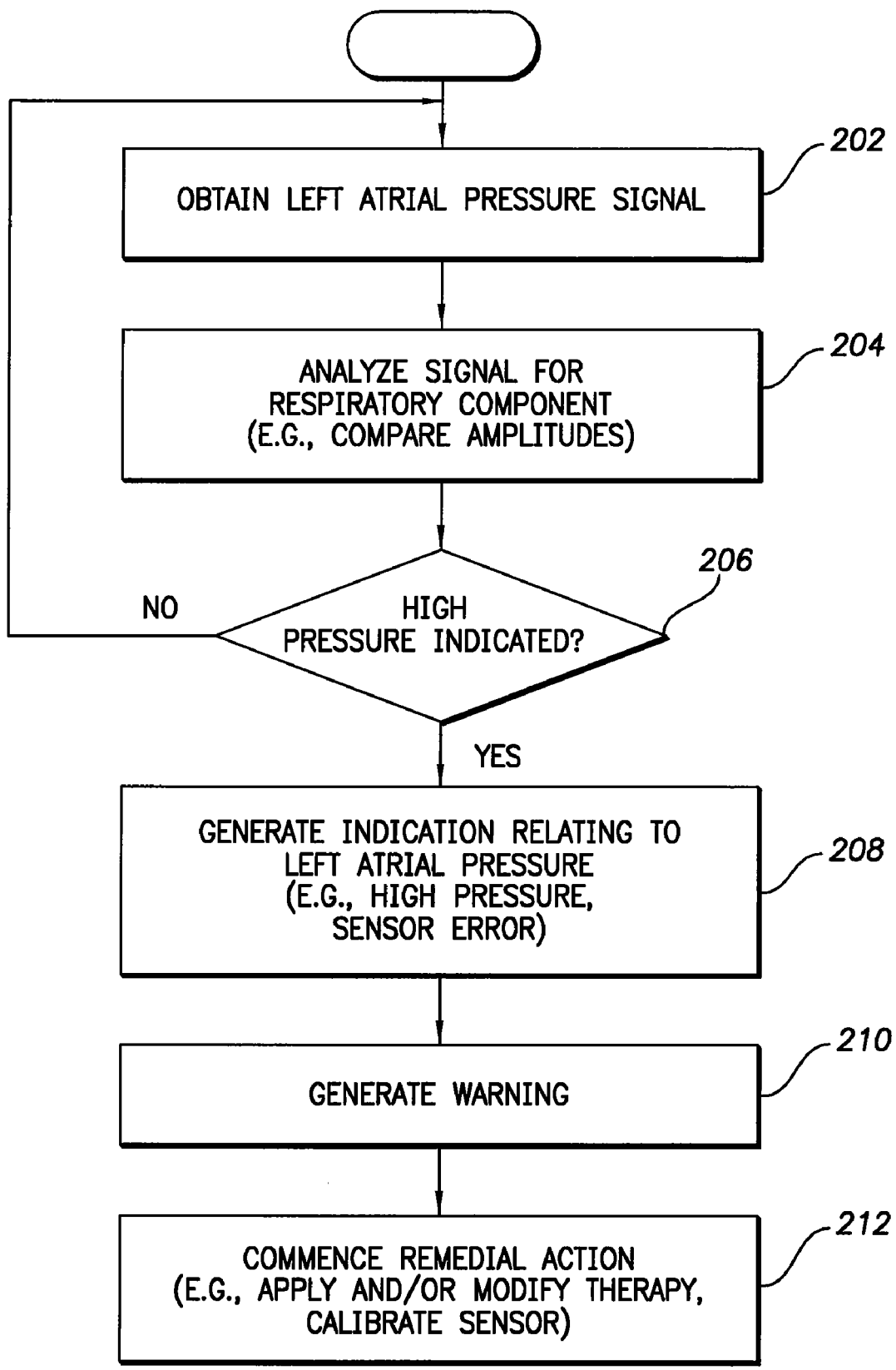
FIG. 2 is a simplified flowchart of an embodiment of operations that may be performed to generate an indication relating to whether a left atrial pressure signal includes a respiratory component.

FIG. 2 illustrates a sample embodiment of operations that may be performed to determine pressure in a left atrium of a patient. For convenience, the operations of FIG. 2 (and any other operations herein) may be described as being performed by specific components. It should be appreciated, however, that these operations may be performed in conjunction with or by other components.

As represented by block 202 initially a pressure signal is obtained via, for example, a pressure sensor implanted in or near the left atrium. Samples of the pressure signal to be analyzed may be collected over a relatively short period of time (e.g., as illustrated in FIG. 1). In addition, the left atrial pressure may be monitored over a longer period of time by collecting the left atrial pressure signal information on a regular basis (e.g., periodically). For example, the left atrial pressure signal may be acquired daily (once a day), weekly, or at other time intervals.

In some embodiments additional factors may be taken into consideration to determine when or whether to measure the left atrial pressure. For example, when attempting to determine whether the left atrial pressure is high due to chronic heart problems, one or more conditions or events may be monitored to ensure that any change in left atrial pressure is not caused by a transient event. In the event such a condition or event is detected at a given point in time, a pressure reading may not be acquired or a reading of high pressure at that point in time may be ignored for purposes of generating a high-pressure warning.

In some embodiments an activity sensor or some other suitable mechanism may be used to monitor the activity level or position of the patient. For example, if the sensed information indicates that the patient is currently relatively active or the patient is not currently in a supine position, the pressure signal may not be collected. Alternatively, the sensed information may be used to determine whether a rise in left atrial pressure is due to increased activity on the part of the patient (e.g., due to exercise, standing up quickly, etc.) rather than reduced function of the left ventricle.

In some embodiments a sensor or some other suitable mechanism (e.g., a data entry system for the patient) may be used to monitor whether the patient is eating or has recently eaten. In this way, it may be determined whether a rise in left atrial pressure is due to these events, or a decision may be made to collect the pressure information for a high left atrial pressure warning test at another time.

In some embodiments a sensor or some other suitable mechanism (e.g., an implantable cardiac device) may be used to monitor other cardiac conditions that may cause elevated left atrial pressure. For example, such a mechanism may be used to determine whether the patient is suffering from congestive heart failure.

As represented by block 204 in FIG. 2, the left atrial pressure signal is analyzed to determine whether the pressure signal includes a respiratory component. As discussed above, in some embodiments this may involve comparing minimum and maximum pressure signals, determining whether the pressure signal includes any appreciable respiratory component or determining whether the amplitude of the respiratory component has changed (e.g., decreased) to a certain degree.

A variety of mechanisms and techniques may be employed to analyze the left atrial pressure signal or employed in conjunction with such analysis. For example, some form of signal filtering may be employed to extract the respiratory signal from the pressure signal. In some embodiments the peak-to-peak amplitude of the respiratory component may be compared to a threshold. In the event the peak-to-peak amplitude drops below the threshold, a determination may be made that the left atrial pressure is no longer being modulated by the patient's respiration. In some implementations this may involve analyzing the daily minimum left atrial pressure swing modulated by respiration.

In some embodiments a sliding window discriminator may be employed to analyze the standard deviation of the amplitude of the respiratory component or the difference between the minimum and maximum signals. In the event the standard deviation drops to a certain degree (e.g., drops to 10% of a baseline value) a determination may be made that the left atrial pressure is no longer being modulated by the patient's respiration to any appreciable degree.

A variety of techniques may be employed to select parameters associated with a lack of or a reduction in a respiratory component. For example, in some embodiments tests may be conducted or models made to determine an expectedly level of respiratory modulation for a given magnitude of left atrial pressure. In some cases these values may be selected based on the condition, anatomy or other circumstances associated with a given patient. For example, in some patients the respiratory component may effectively disappear above 20 mmHg while on other patients the respiratory component may disappear above 25 mmHg.

As represented by block 206 in FIG. 2, based on the analysis of the respiratory component a determination is made as to whether the pressure in the left atrium is higher than normal. If no such indication is made, the process of regularly monitoring the left atrial pressure continues at block 202.

In some embodiment high pressure may be indicated when the pressure in the left atrium is on the order of 25-30 mmHg or higher. As mentioned above, such a determination may be made, for example, by comparing minimum and maximum pressure values or by determining a magnitude value or a reduction in the magnitude of the respiratory component that corresponds to this level of pressure. In these cases, a threshold may be set to a small delta value (e.g., 1 mmHg) for the operations involving comparison of the minimum and maximum values, or to a magnitude value (e.g., 1 mmHg peak-to-peak) or to a reduction in magnitude (e.g., 80%) for operations involving the magnitude of the respiratory component. Then, when the minimum/maximum difference exceeds the threshold value, or when the magnitude of the measured respiratory component falls below the magnitude threshold or drops by an amount that exceeds the percentage threshold, it may be determined that the pressure in the left atrium is higher than normal. In practice, any of the parameters mentioned above may vary from patient to patient. Thus, the thresholds for a given patient may be defined accordingly.

As represented by block 208, if a lack of or a reduction in a respiratory component indicates that the left atrial pressure is higher than normal, an indication may be generated relating to the left atrial pressure. In some embodiments the indication simply indicates that the left atrial pressure is high. Such an indication may be made irrespective of whether the pressure sensor is properly calibrated since the indication is based on the presence or absence of a respiratory component in the pressure signal, not the magnitude of the pressure signal.

In some embodiments an indication of heart failure may be generated based on the above operations. For example, if the left atrial pressure remains elevated for a given period of time (e.g., several days), an indication of heart failure (e.g., acute decompensation heart failure) may be generated. Here, one or more thresholds may be employed relating to the length of time the left atrial pressure needs to be high to generate an indication, the percentage of time over that time period the left atrial period needs to be high, or the extent (e.g., relative magnitude) of the increase in left atrial pressure that is designated as "elevated" pressure for purposes of generating a heart failure indication.

In other embodiments the indication may serve as a basis for determining whether there is a sensor error. These embodiments are discussed in more detail below in conjunction with FIG. 3.

As represented by block 210, a warning signal may be generated in conjunction with the generation of the indication. For example, in some embodiments a warning actuator may generate a mechanical signal such as an audible signal or a vibratory signal. Such a signal may indicate, for example, that the patient should have a checkup, should take previously prescribed medication, or take some other action. In some embodiments the warning may be generated by an electrode circuit that generates electrical signals such as a tissue tickler signal or a radio frequency signal (e.g., to send an indication to a device external to the patient).

As represented by block 212, in some embodiments remedial action may be taken in conjunction with the generation of the indication. For example, therapy may be applied to the patient and/or therapy for the patient may be modified in response to the indication. In some embodiments, a drug dispenser supplies a drug (e.g., a diuretic) to the patient in an attempt to treat fluid overloading in the lungs.

In some embodiments remedial action may involve calibrating the pressure sensor. This action may be necessary in the event that a sensor error was detected at block 208. These and other aspects relating to determining whether there is a sensor error will now be treated in conjunction with FIG. 3.

As represented by block 302, a determination as to whether a sensor is operating properly involves obtaining a reading of the pressure value measured by the sensor. This may involve, for example, acquiring or generating values (e.g., in mmHg) of the pressure in the left atrium by processing the signals from the sensor.

The process of checking the operation of the left atrial pressure sensor may be invoked at various times. In some embodiments this process may be invoked in response to an indication that the pressure in the left atrium is high (e.g., from block 208 in FIG. 2). In some embodiments, the sensor check process may be invoked first, followed by an analysis of the respiratory component of the pressure signal. Such a sensor check may be performed regularly (e.g., periodically) or based on some form of stimulus (e.g., abnormal pressure readings).

In some embodiments, the calibration of a sensor is commenced at a time when the left atrial pressure signal is about to lose the respiration pattern. For example, the process may be initiated by determining whether the patient is currently exercising, eating, or experiencing an episode related to congestive heart failure. These conditions or events may be monitored in a similar manner as discussed above. The calibration validation process may be invoked during a transition between a time when the left atrial pressure signal has a respiratory component and a time when the left atrial pressure signal does not have a respiratory component, or vice versa. For example, the left atrial pressure may be measured at a first point in time when an amplitude of the signal component relating to respiration is below a first threshold and at a second point in time when the amplitude of the signal component relating to respiration is above a second threshold. In some cases the first and second threshold may comprise the same value (e.g., 20 mmHg). Examples of the above transitions are illustrated by the portions of FIG. 1 associated with beats 55 to 62 and beats 90 to 95.

As discussed above in conjunction with block 208, in some embodiments a sensor check is performed in conjunction with the generation of a high left atrial pressure indication. In such a case, the pressure reading may be derived from the pressure signal that resulted in the generation of the high-pressure indication. For example, the pressure reading may be obtained by determining the pressure level represented by the portion of the pressure signal that does not have respiratory modulation.

Figure 3:
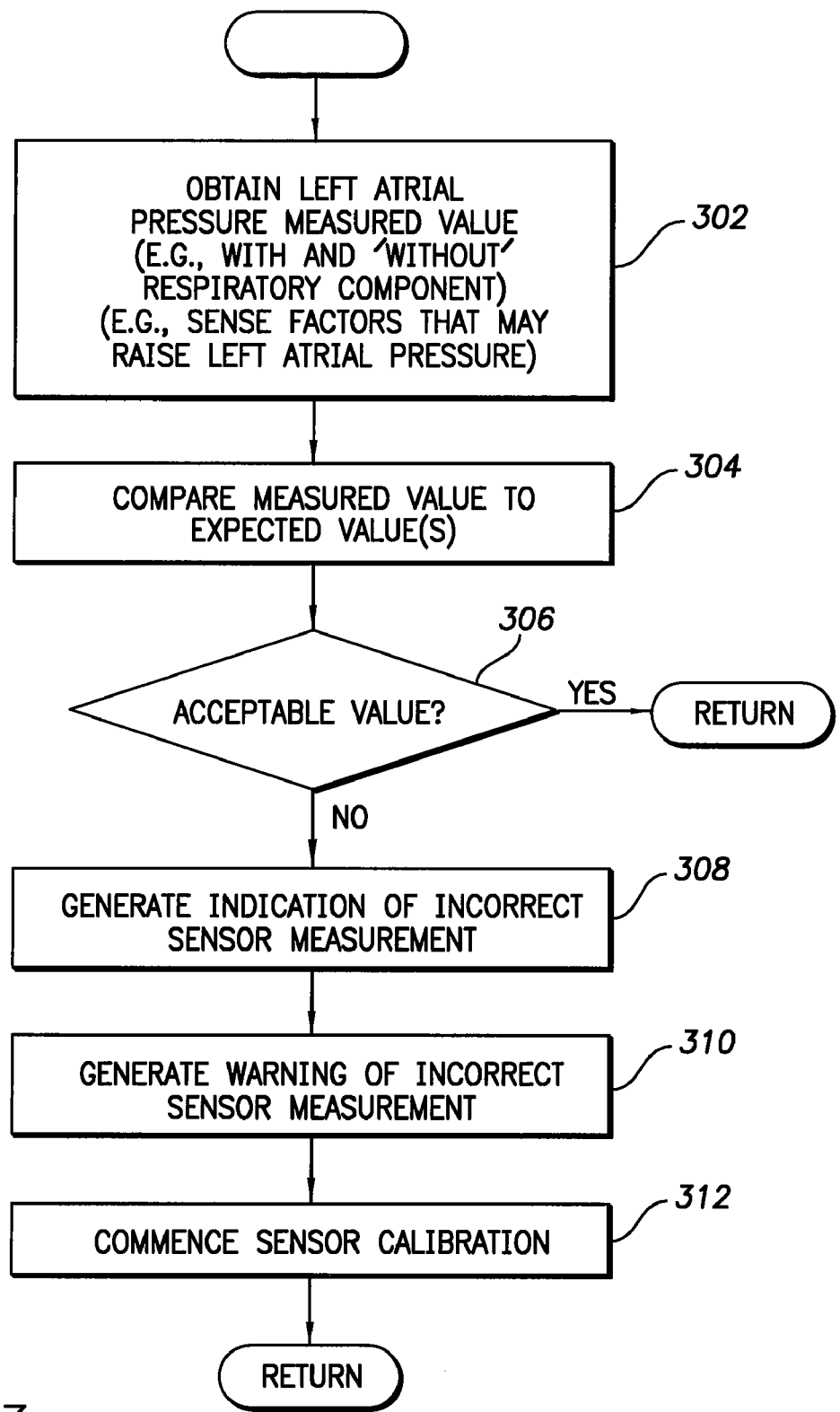
FIG. 3 is a simplified flowchart of an embodiment of operations that may be performed to determine whether a left atrial pressure sensor is generating erroneous readings.

As represented by block 304 in FIG. 3, the measured pressure value may be compared with one or more expected values (e.g., a threshold). For example, an indication at block 208 of FIG. 2 may indicate that the pressure in the left atrium is on the order of 25 to 30 mmHg or more. Hence, at block 304 the measured pressure value may be compared to a threshold set to, for example, 25 mmHg.

As represented by block 306, in the event the measured pressure value is at an acceptable level with respect to the expected value or expected values, the process of regularly monitoring the left atrial pressure continues (e.g., at block 202 in FIG. 2). This may be the case, for example, when the measured pressure value is above a threshold (e.g., 25 mmHg). Alternatively, the measured pressure value may be compared with an acceptable range defined by two thresholds, including a lower limit (e.g., on the order of 25 mmHg) and a practical upper limit (e.g., on the order of 40 to 45 mmHg).

As represented by block 308, in the event the measured pressure value is not at an acceptable level with respect to the expected value or expected values, an indication of an incorrect sensor measurement may be generated. Such an indication may be generated, for example, when the measure pressure value is below a lower threshold (e.g., on the order of 25 mmHg) or above an upper threshold (e.g., on the order of 40 to 45 mmHg).

As represented by block 310, a warning signal may be generated in conjunction with the generation of the indication. For example, in some embodiments a warning actuator may generate a mechanical signal such as an audible signal or a vibratory signal. Such a signal may indicate, for example, that the patient should have the sensor checked by a physician or technician, or should take some other action. In some embodiments the warning may be generated by an electrode circuit that generates electrical signals such as a tissue tickler signal or a radio frequency signal (e.g., to send an indication to a device external to the patient).

As represented by block 312, in some embodiments remedial action may be taken in conjunction with the generation of the indication. For example, in some embodiments operations may be invoked in an attempt to calibrate the pressure sensor. Such an operation may be performed automatically or in conjunction with the patient, some other person or some other apparatus. In some embodiments the calibration procedure may involve a Valsalva maneuver performed by the patient.

Exemplary Cardiac Device

With the above description in mind, additional details of monitoring left atrial pressure will be discussed in conjunction with a specific example where monitoring is performed by an implantable cardiac device (e.g., a stimulation device such as an implantable cardioverter defibrillator, a pacemaker, etc.). Here, one or more of the components and operations described above may be implemented in or in conjunction with such an implantable cardiac device. It should be appreciated that this example is provided for explanatory purposes and that monitoring may be implemented using other types of devices. It also should be appreciated and understood that other cardiac devices, including those that are not necessarily implantable, may be used in conjunction with the teachings herein.

Figure 4:
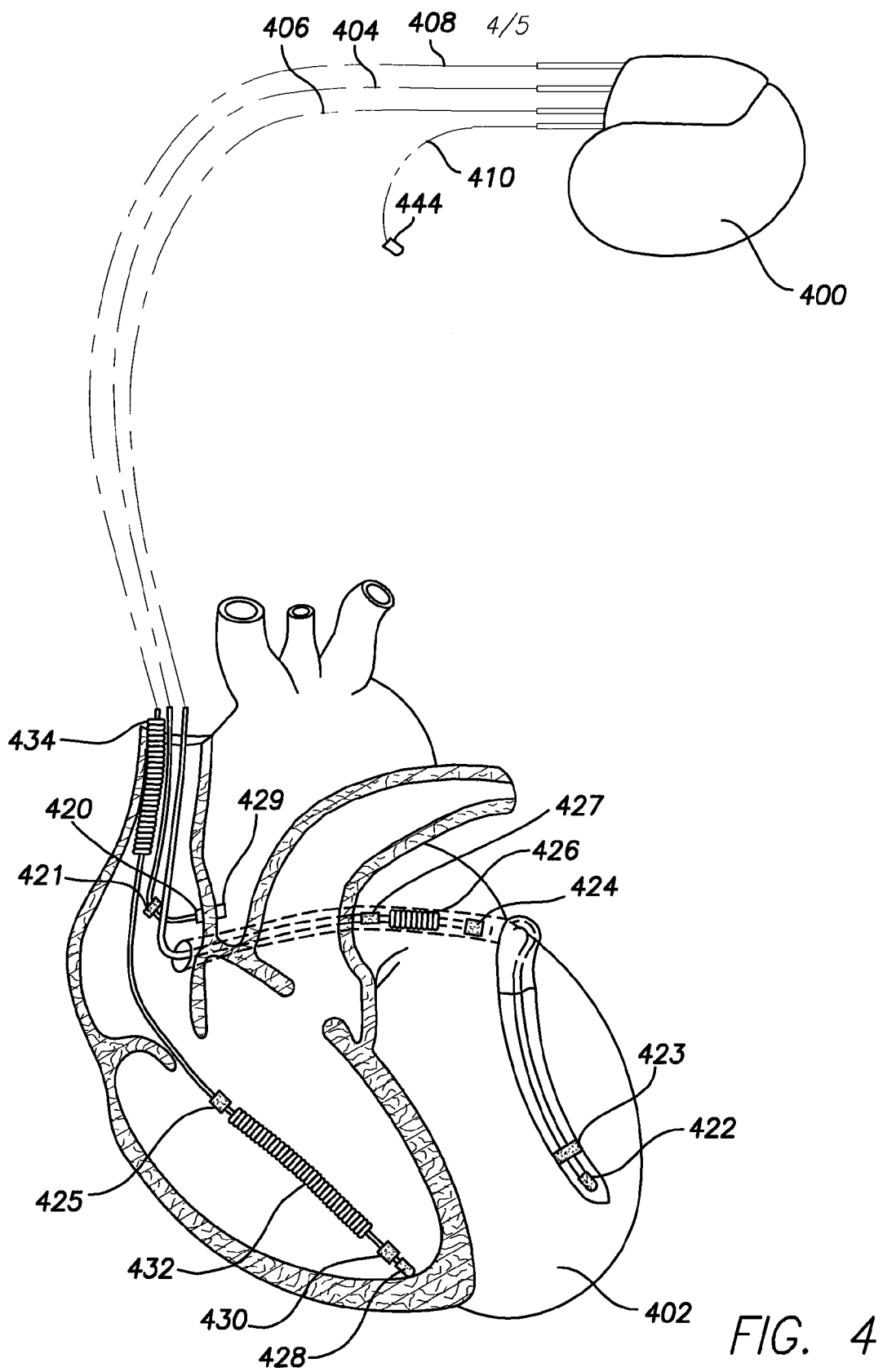
FIG. 4 is a simplified diagram of an embodiment of an implantable stimulation device in electrical communication with one or more leads implanted in a patient's heart for sensing conditions in the patient, delivering therapy to the patient, or providing some combination thereof.

FIG. 4 illustrates an exemplary implantable cardiac device 400 in electrical communication with a patient's heart 402 by way of three leads 404, 406, and 408, suitable for delivering multi-chamber stimulation and shock therapy. To sense atrial cardiac signals and to provide right atrial chamber stimulation therapy, the device 400 is coupled to an implantable right atrial lead 404 having, for example, an atrial tip electrode 420, which typically is implanted in the patient's right atrial appendage or septum. FIG. 4 also shows the right atrial lead 404 as having an optional atrial ring electrode 421.

To sense left atrial and ventricular cardiac signals and to provide left chamber pacing therapy, device 400 is coupled to a coronary sinus lead 406 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 406 is designed to receive atrial and ventricular cardiac signals and to deliver left ventricular pacing therapy using, for example, a left ventricular tip electrode 422 and, optionally, a left ventricular ring electrode 423; provide left atrial pacing therapy using, for example, a left atrial ring electrode 424; and provide shocking therapy using, for example, a left atrial coil electrode 426 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

Device 400 is also shown in electrical communication with the patient's heart 402 by way of an implantable right ventricular lead 408 having, in this implementation, a right ventricular tip electrode 428, a right ventricular ring electrode 430, a right ventricular (RV) coil electrode 432 (or other electrode capable of delivering a shock), and a superior vena cava (SVC) coil electrode 434 (or other electrode capable of delivering a shock). Typically, the right ventricular lead 408 is transvenously inserted into the heart 402 to place the right ventricular tip electrode 428 in the right ventricular apex so that the RV coil electrode 432 will be positioned in the right ventricle and the SVC coil electrode 434 will be positioned in the superior vena cava. Accordingly, the right ventricular lead 408 is capable of sensing or receiving cardiac signals, and delivering stimulation in the form of pacing and shock therapy to the right ventricle.

The leads 404, 406 and 408 also may include one or more pressure sensors for measuring pressure in a chamber or vessel of the heart H. In a typical embodiment, the right atrial lead 404 or some other lead may be implanted in the septal wall (e.g., in the area of the fossa ovalis) separating the right atrium and the left atrium to measure pressure in the left atrium. For example, the lead 404 may include a pressure sensor 429 located on a distal portion of the lead. Alternatively, the pressure sensor 429 may be located at some other location along the lead and coupled to receive pressure waves from the left atrium. In some embodiments, a pressure sensor 427 on the lead 406 may be adapted to measure pressure in the left atrium. It should be appreciated that other mechanisms may be employed to measure pressure in a given chamber or vessel.

A pressure sensor 425 on the lead 408 may measure pressure in the right ventricle. In some embodiments readings from a pressure sensor in one chamber or vessel may be used to help calibrate the readings of another pressure sensor and another chamber or vessel.

Device 400 is also shown in electrical communication with a lead 410 including one or more components 444 such as a physiologic sensor. The component 444 may be positioned in, near or remote from the heart.

It should be appreciated that the device 400 may connect to leads other than those specifically shown. In addition, the leads connected to the device 400 may include components other than those specifically shown. For example, a lead may include other types of electrodes, sensors or devices that serve to otherwise interact with a patient or the surroundings.

Figure 5:
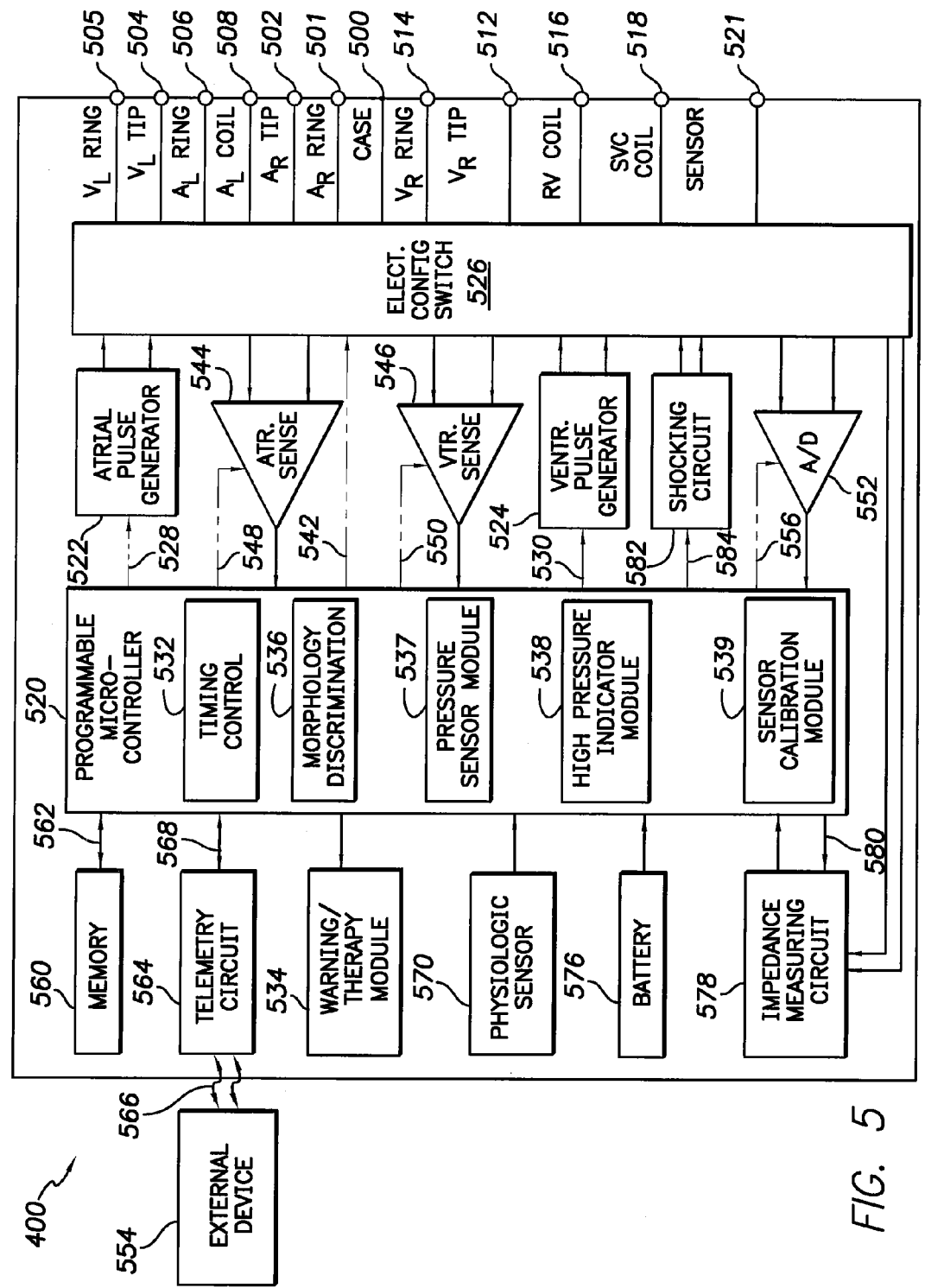
FIG. 5 is a simplified functional block diagram of an embodiment of an implantable cardiac device, illustrating basic elements that may be configured to sense conditions in the patient, deliver therapy to the patient, or provide some combination thereof.

FIG. 5 depicts an exemplary, simplified block diagram illustrating sample components of the cardiac device 400. The device 400 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 500 for device 400 is often referred to as the "can", "case" or "case electrode", and may be programmably selected to act as the return electrode for all "unipolar" modes. Housing 500 may further be used as a return electrode alone or in combination with one or more of the coil electrodes 426, 432 and 434 for shocking purposes. Housing 500 further includes a connector (not shown) having a plurality of terminals 501, 502, 504, 505, 506, 508, 512, 514, 516 and 518 (shown schematically and, for convenience, the names of the electrodes to which they are connected are shown next to the terminals). The connector may be configured to include various other terminals depending on the requirements of a given application. For example, in some embodiments the connector may include one or more terminals 521 that connect to one or more external sensors (e.g., one or more pressure sensors as discussed herein, not shown in FIG. 5).

To achieve right atrial sensing and pacing, the connector includes, for example, a right atrial tip terminal (AR TIP) 502 adapted for connection to the right atrial tip electrode 420. A right atrial ring terminal (AR RING) 501 may also be included and adapted for connection to the right atrial ring electrode 421. To achieve left chamber sensing, pacing, and shocking, the connector includes, for example, a left ventricular tip terminal (VL TIP) 504, a left ventricular ring terminal (VL RING) 505, a left atrial ring terminal (AL RING) 506, and a left atrial shocking terminal (AL COIL) 508, which are adapted for connection to the left ventricular tip electrode 422, the left ventricular ring electrode 423, the left atrial ring electrode 424, and the left atrial coil electrode 426, respectively.

To support right chamber sensing, pacing, and shocking, the connector further includes a right ventricular tip terminal (VR TIP) 512, a right ventricular ring terminal (VR RING)

514, a right ventricular shocking terminal (RV COIL) 516, and a superior vena cava shocking terminal (SVC COIL) 518, which are adapted for connection to the right ventricular tip electrode 428, the right ventricular ring electrode 430, the RV coil electrode 432, and the SVC coil electrode 434, respectively.

At the core of the device 400 is a programmable microcontroller 520 that controls the various modes of stimulation therapy. As is well known in the art, microcontroller 520 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 520 includes the ability to process or monitor input signals (data or information) as controlled by a program code stored in a designated block of memory. The type of microcontroller is not critical to the described implementations. Rather, any suitable microcontroller 520 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 5 also shows an atrial pulse generator 522 and a ventricular pulse generator 524 that generate pacing stimulation pulses for delivery by the right atrial lead 404, the coronary sinus lead 406, and the right ventricular lead 408 via an electrode configuration switch 526. It is understood that in order to provide stimulation therapy in each of the four chambers of the heart, the atrial and ventricular pulse generators 522 and 524 may include dedicated, independent pulse generators, multiplexed pulse generators, or shared pulse generators. The pulse generators 522 and 524 are controlled by the microcontroller 520 via appropriate control signals 528 and 530, respectively, to trigger or inhibit the stimulation pulses.

Microcontroller 520 further includes timing control circuitry 532 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 520 further includes an arrhythmia detector (not shown). The arrhythmia detector may be utilized by the device 400 for determining desirable times to administer various therapies. The arrhythmia detector may be implemented, for example, in hardware as part of the microcontroller 520, or as software/firmware instructions programmed into the device and executed on the microcontroller 520 during certain modes of operation.

Microcontroller 520 may include a morphology discrimination module 536, a capture detection module (not shown) and an auto sensing module (not shown). These modules are optionally used to implement various exemplary recognition algorithms and/or methods. The aforementioned components may be implemented, for example, in hardware as part of the microcontroller 520, or as software/firmware instructions programmed into the device and executed on the microcontroller 520 during certain modes of operation.

The electrode configuration switch 526 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 526, in response to a control signal 542 from the microcontroller 520, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 544 and ventricular sensing circuits (VTR. SENSE) 546 may also be selectively coupled to the right atrial lead 404, coronary sinus lead 406, and the right ventricular lead 408, through the switch 526 for detecting the presence of cardiac activity in each of the four chambers of the heart. Accordingly, the atrial and ventricular sensing circuits 544 and 546 may include dedicated sense amplifiers, multiplexed amplifiers, or shared amplifiers. Switch 526 determines the "sensing polarity" of the cardiac signal by selectively closing the appropriate switches, as is also known in the art. In this way, the clinician may program the sensing polarity independent of the stimulation polarity. The sensing circuits (e.g., circuits 544 and 546) are optionally capable of obtaining information indicative of tissue capture.

Each sensing circuit 544 and 546 preferably employs one or more low power, precision amplifiers with programmable gain and/or automatic gain control, bandpass filtering, and a threshold detection circuit, as known in the art, to selectively sense the cardiac signal of interest. The automatic gain control enables the device 400 to deal effectively with the difficult problem of sensing the low amplitude signal characteristics of atrial or ventricular fibrillation.

The outputs of the atrial and ventricular sensing circuits 544 and 546 are connected to the microcontroller 520, which, in turn, is able to trigger or inhibit the atrial and ventricular pulse generators 522 and 524, respectively, in a demand fashion in response to the absence or presence of cardiac activity in the appropriate chambers of the heart. Furthermore, as described herein, the microcontroller 520 is also capable of analyzing information output from the sensing circuits 544 and 546 and/or a data acquisition system 552. This information may be used to determine or detect whether and to what degree tissue capture has occurred and to program a pulse, or pulses, in response to such determinations. The sensing circuits 544 and 546, in turn, receive control signals over signal lines 548 and 550, respectively, from the microcontroller 520 for purposes of controlling the gain, threshold, polarization charge removal circuitry (not shown), and the timing of any blocking circuitry (not shown) coupled to the inputs of the sensing circuits 544 and 546 as is known in the art.

For arrhythmia detection, the device 400 utilizes the atrial and ventricular sensing circuits 544 and 546 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector (not shown) of the microcontroller 520 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 552. The data acquisition system 552 is configured (e.g., via signal line 556) to acquire intracardiac electrogram ("IEGM") signals or other signals, convert the raw analog data into a digital signal, and store the digital signals for later processing and/or telemetric transmission to an external device 554. For example, the data acquisition system 552 may be coupled to the right atrial lead 404, the coronary sinus lead 406, the right ventricular lead 408 and other leads through the switch 526 to sample cardiac signals across any pair of desired electrodes.

The data acquisition system 552 also may be coupled to receive signals from other input devices. For example, the data acquisition system 552 may sample signals from a physiologic sensor 570 or other components shown in FIG. 5 (connections not shown).

The microcontroller 520 is further coupled to a memory 560 by a suitable data/address bus 562, wherein the programmable operating parameters used by the microcontroller 520 are stored and modified, as required, in order to customize the operation of the device 400 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 402 within each respective tier of therapy. One feature of the described embodiments is the ability to sense and store a relatively large amount of data (e.g., from the data acquisition system 552), which data may then be used for subsequent analysis to guide the programming of the device.

Advantageously, the operating parameters of the implantable device 400 may be non-invasively programmed into the memory 560 through a telemetry circuit 564 in telemetric communication via communication link 566 with the external device 554, such as a programmer, transtelephonic transceiver, a diagnostic system analyzer or some other device. The microcontroller 520 activates the telemetry circuit 564 with a control signal (e.g., via bus 568). The telemetry circuit 564 advantageously allows intracardiac electrograms and status information relating to the operation of the device 400 (as contained in the microcontroller 520 or memory 560) to be sent to the external device 554 through an established communication link 566.

The device 400 can further include one or more physiologic sensors 570. In some embodiments the device 400 may include a "rate-responsive" sensor that may provide, for example, information to aid in adjustment of pacing stimulation rate according to the exercise state of the patient. One or more physiologic sensors 570 (e.g., a pressure sensor) may further be used to detect changes in cardiac output, changes in the physiological condition of the heart, or diurnal changes in activity (e.g., detecting sleep and wake states). Accordingly, the microcontroller 520 responds by adjusting the various pacing parameters (such as rate, AV Delay, V-V Delay, etc.) at which the atrial and ventricular pulse generators 522 and 524 generate stimulation pulses.

While shown as being included within the device 400, it is to be understood that a physiologic sensor 570 may also be external to the device 400, yet still be implanted within or carried by the patient. Examples of physiologic sensors that may be implemented in conjunction with device 400 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 570 may optionally include sensors to help detect movement (via, e.g., a position sensor) and/or minute ventilation (via an MV sensor) in the patient. Signals generated by the position sensor and MV sensor may be passed to the microcontroller 520 for analysis in determining whether to adjust the pacing rate, etc. The microcontroller 520 may thus monitor the signals for indications of the patient's position and activity status, such as whether the patient is climbing up stairs or descending down stairs or whether the patient is sitting up after lying down.

The device 400 additionally includes a battery 576 that provides operating power to all of the circuits shown in FIG. 5. For a device 400 which employs shocking therapy, the battery 576 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 576 also desirably has a predictable discharge characteristic so that elective replacement time can be detected. Accordingly, the device 400 preferably employs lithium or other suitable battery technology.

The device 400 can further include magnet detection circuitry (not shown), coupled to the microcontroller 520, to detect when a magnet is placed over the device 400. A magnet may be used by a clinician to perform various test functions of the device 400 and/or to signal the microcontroller 520 that the external device 554 is in place to receive data from or transmit data to the microcontroller 520 through the telemetry circuit 564.

The device 400 further includes an impedance measuring circuit 578 that is enabled by the microcontroller 520 via a control signal 580. The known uses for an impedance measuring circuit 578 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 400 has been implanted; measuring stroke volume; and detecting the opening of heart valves, etc. The impedance measuring circuit 578 is advantageously coupled to the switch 526 so that any desired electrode may be used.

In the case where the device 400 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 520 further controls a shocking circuit 582 by way of a control signal 584. The shocking circuit 582 generates shocking pulses of low (e.g., up to 0.5 J), moderate (e.g., 0.5 J to 10 J), or high energy (e.g., 11 J to 40 J), as controlled by the microcontroller 520. Such shocking pulses are applied to the patient's heart 402 through, for example, two shocking electrodes and as shown in this embodiment, selected from the left atrial coil electrode 426, the RV coil electrode 432, and/or the SVC coil electrode 434. As noted above, the housing 500 may act as an active electrode in combination with the RV coil electrode 432, and/or as part of a split electrical vector using the SVC coil electrode 434 or the left atrial coil electrode 426 (i.e., using the RV electrode as a common electrode).

Cardioversion level shocks are generally considered to be of low to moderate energy level (so as to minimize pain felt by the patient), synchronized with an R-wave, pertaining to the treatment of tachycardia, or some combination the above. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 520 is capable of controlling the synchronous or asynchronous delivery of the shocking pulses.

The device 400 also includes several other components that provide functionality relating to monitoring left atrial pressure. For example, the microcontroller 520 (e.g., incorporating signal processing functionality) may include a pressure sensor module 537 that incorporates functionality for processing pressure signals (e.g., as discussed above). The microcontroller 520 may include a high pressure indicator module 538 that incorporates functionality relating to generating an indication of high left atrial pressure (e.g., as discussed above). The microcontroller 520 may include a sensor calibration module 539 that incorporates functionality relating to determining whether a sensor is providing proper readings and, in the event it is not, initiating or performing a calibration procedure (e.g., as discussed above). The device 500 also may include a warning/therapy module 534 adapted to generate warning signals and/or administer therapy as discussed above. These and other components described herein may be incorporated into an implantable medical device (e.g., a monitoring device), an implantable cardiac device (e.g., a cardiac stimulation device) or any other suitable device in accordance with the requirements of a given application.

It should be appreciated that various modifications may be incorporated into the disclosed embodiments based on the teachings herein. For example, the structure and functionality taught herein may be incorporated into different types of devices other than those types specifically described. In addition, the various signals described herein and/or other signals may be sensed in other ways and using different sensing components. Such sensors (e.g., electrodes, physiologic sensors, etc.) also may be incorporated into other types of implantable leads or may be implanted or otherwise provided without the use of leads (e.g., via a wireless component). These sensors may be located at various positions throughout the heart or the body. Various algorithms and/or techniques may be employed to determine whether and to what degree a respiratory signal modulates left atrial pressure.

It should be appreciated from the above that the various structures and functions described herein may be incorporated into a variety of apparatuses (e.g., a stimulation device, a lead, a monitoring device, etc.) and implemented in a variety of ways. Different embodiments of the stimulation device may include a variety of hardware and software processing components. In some embodiments, hardware components such as processors, controllers, state machines and/or logic may be used to implement the described components or circuits.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may simply send raw data or processed data to an external device that then performs the necessary processing.

The components and functions described herein may be connected and/or coupled in many different ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of analyzing left atrial pressure of a patient, comprising:
   obtaining at least one signal from the patient that is representative of the patient's left atrial pressure, the at least one signal having a respiration component related to the respiration of the patient;
   analyzing the at least one signal with a programmable microcontroller configured to assess whether the respiratory component is present in the at least one signal;
   determining with the programmable microcontroller whether the left atrial pressure is above a threshold when the respiratory component is assessed to not be present in the at least one signal; and applying therapy to the patient or modifying therapy for the patient in response to the left atrial pressure exceeding the threshold when the respiratory component is assessed to not be present in the at least one signal.

2. The method of claim 1, further comprising generating a warning of at least one of the group consisting of: high left atrial pressure, reduced left ventricle function, fluid accumulation in lungs of the patient, and heart failure if the left atrial pressure is above the threshold.

3. The method of claim 1, wherein analyzing further comprises comparing an amplitude of the respiratory component relating to the respiration of the patient with an amplitude of a respiration threshold.

4. The method of claim 1, wherein analyzing further comprises determining whether an amplitude of the respiratory component relating to the respiration of the patient has decreased.

5. The method of claim 1, wherein:
the at least one signal comprises a minimum left atrial pressure signal and a maximum left atrial pressure signal; and
analyzing further comprises comparing a difference between the minimum and maximum left atrial pressure signals with a threshold.

6. The method of claim 1, further comprising at least one of the group of: storing a parameter in a data memory, generating an audible signal, generating a vibratory signal, and generating a radio frequency signal.

7. The method of claim 1, further comprising:
obtaining a measured value of the left atrial pressure; and
comparing the measured value with the threshold.

8. The method of claim 7, further comprising generating, based on the comparing, a warning of an incorrect left atrial pressure sensor measurement.

9. The method of claim 7, further comprising calibrating a left atrial pressure sensor when the at least one signal transitions between a time containing the respiratory component and a time not containing the respiratory component or vice versa.

10. The method of claim 7, wherein the measured value is obtained between a first point in time when an amplitude of the respiratory component relating to the respiration of the patient is below a first threshold and a second point in time when the amplitude of the respiratory component relating to the respiration of the patient is above a second threshold.

11. The method of claim 7, wherein the measured value is obtained during exercise, after eating, or during a congestive heart failure episode.

12. An apparatus for analyzing left atrial pressure of a patient, comprising:
an implantable pressure sensor adapted to obtain at least one signal from the patient that is representative of the patient's left atrial pressure, the at least one signal having a respiratory component related to the respiration of the patient; and
a processor adapted to analyze the at least one signal to assess whether the respiratory component related to the respiration of the patient is present, and determining whether the left atrial pressure is above a threshold when the at least one signal is assessed to not contain the respiratory component relating to the respiration of the patient.

13. The apparatus of claim 12, wherein the processor is further adapted to generate a warning of at least one of the group of: high left atrial pressure, reduced left ventricle function, fluid accumulation in lungs of the patient, and heart failure.

14. An implantable system for analyzing left atrial pressure of a patient, the system comprising:
means for obtaining at least one signal representative of left atrial pressure, the at least one signal having a respiratory component related to the respiration of the patient;
means for analyzing the at least one signal for assessing whether the respiratory component related to the respiration of the patient is present; and
means for determining whether the left atrial pressure is above a threshold when the at least one signal is assessed to not contain the respiratory component relating to the respiration of the patient.

* * * * *